US00PP15117P2

(12) United States Plant Patent
Trees

(10) Patent No.: US PP15,117 P2
(45) Date of Patent: Aug. 31, 2004

(54) SCAEVOLA PLANT NAMED 'BALSCAVBON'

(50) Latin Name: *Scaevola humilas*
Varietal Denomination: Balscavbon

(75) Inventor: Scott C. Trees, Shell Beach, CA (US)

(73) Assignee: Ball Horticultural Co., West Chicago, IL (US)

( * ) Notice: Subject to any disclaimer, the term of this patent is extended or adjusted under 35 U.S.C. 154(b) by 0 days.

(21) Appl. No.: 10/602,104

(22) Filed: Jun. 23, 2003

(51) Int. Cl.[7] ..... A01H 5/00
(52) U.S. Cl. ..... Plt./363
(58) Field of Search ..... Plt./363

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Scaevola plant named Balscavbon, characterized by its upright and outwardly spreading plant habit; freely branching growth habit; medium green-colored leaves; and numerous violet-colored flowers.

1 Drawing Sheet

Botanical classification/cultivar designation: *Scaevola humilas* cultivar Balscavbon.

BACKGROUND OF THE INVENTION

The present Invention relates to a new and distinct cultivar of Scaevola plant, botanically known as *Scaevola humilas* and hereinafter referred to by the cultivar name 'Balscavbon'.

The new Scaevola is a product of a planned breeding program conducted by the Inventor in Arroyo Grande, Calif. The objective of the breeding program was to develop new Scaevola cultivars with freely branching growth habit and attractive flower and foliage coloration.

The new Scaevola originated from an open-pollination made by the Inventor in November, 2000, of unnamed proprietary *Scaevola humilas* selections, not patented. The cultivar Balscavbon was discovered and selected by the Inventor as a flowering plant within the progeny of the stated open-pollination in a controlled environment in Arroyo Grande, Calif. in 2000.

Asexual reproduction of the new cultivar by terminal cuttings taken at Arroyo Grande, Calif. since 2000, has shown that the unique features of this new Scaevola are stable and reproduced true to type in successive generations of asexual reproduction.

SUMMARY OF THE INVENTION

The following traits have been repeatedly observed and are determined to be the unique characteristics of 'Balscavbon'. These characteristics in combination distinguish 'Balscavbon' as a new and distinct cultivar:

1. Upright and outwardly spreading plant habit.
2. Freely branching growth habit.
3. Medium green-colored leaves.
4. Numerous violet-colored flowers.

Plants of the new Scaevola differ from plants of the parent selections primarily in flower color and plant habit.

Plants of the new Scaevola can also be compared to plants of the cultivar Blue Wonder, disclosed in U.S. Plant Pat. No. 7,929. In side-by-side comparisons conducted by the Inventor in Arroyo Grande, Calif., plants of the new Scaevola and the cultivar Blue Wonder differed in the following characteristics:

1. Plants of the new Scaevola were more compact than plants of the cultivar Blue Wonder.
2. Plants of the new Scaevola were more freely branching than plants of the cultivar Blue Wonder.
3. Plants of the new Scaevola had smaller leaves with shorter petioles than plants of the cultivar Blue Wonder.
4. Plants of the new Scaevola had smaller flowers than plants of the cultivar Blue Wonder.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Scaevola.

The photograph at the top of the sheet comprises a side perspective view of typical plants of 'Balscavbon'.

The photograph at the bottom of the sheet is a close-up view of a typical inflorescence of 'Balscavbon'.

DETAILED BOTANICAL DESCRIPTION

Plants used in the aforementioned photographs and for the following description were grown under conditions which closely approximate commercial production conditions in a polycarbonate-covered greenhouse in West Chicago, Ill. Plants were about 9 weeks from planting rooted cuttings in 10-cm containers. During the production of the plants, the day temperatures ranged from 24 to 26° C., night temperatures ranged from 15 to 18° C., and light levels ranged from 5,000 to 9,000 footcandles.

In the following description, color references are made to The Royal Horticultural Society Colour Chart, 2001 Edition, except where general terms of ordinary dictionary significance are used.

Botanical classification: *Scaevola humilas* cultivar Balscavbon.

Parentage: Open-pollination of unnamed proprietary *Scaevola humilas* selections, not patented.

Propagation:

*Type cutting.*—Terminal cuttings.

*Time to initiate roots.*—About 7 days at 18° C.

*Time to develop roots.*—About three weeks at 18° C.

*Rooting habit.*—Fibrous and freely branching.

Plant description:

*Plant form and growth habit.*—Annual container and garden plant. Upright and outwardly spreading plant habit; plants eventually become more spreading and trailing with development. Freely branching with about nine lateral branches per plant.

*Plant height (soil level to top of plant plane).*—About 15.8 cm.

*Plant width or spread.*—About 39.2 cm.

*Lateral branch description.*—Length: About 21.4 cm. Diameter: About 2 mm. Internode length: About 1.2 cm. Texture: Pubescent. Color: 144B.

*Foliage description.*—Arrangement: Alternate, simple. Length: About 2.8 cm. Width: About 1.3 cm. Shape: Spatulate. Apex: Acute. Base: Attenuate. Margin: Irregularly serrated, slightly serrated towards base and more strongly serrated towards apex. Texture, upper surface: Moderately pubescent. Texture, lower surface: Pubescence along midvein. Color, upper surface: 147A. Color, lower surface: 146A. Venation, upper and lower surfaces: 146B. Petiole length: About 4.4 mm. Petiole diameter: About 2.6 mm. Petiole texture: Densely pubescent. Petiole color: 146B.

Flower description:

*Flower type and shape.*—Zygomorphic, semi-circular, fan-shaped flowers with five petals fused at the base to form a tubular flower throat. Flower throat open along the upper surface exposing reproductive organs. Flowers persistent. No fragrance detected.

*Flower arrangement and quantity.*—Solitary flowers arise from leaf axils with one flower per axil. Flowers held outwardly on upturned lateral apices. Freely flowering, typically about twelve open flowers and flower buds per inflorescence.

*Flowering time.*—Plants flower continuously from May until frost. Flowers typically last at least four days on the plant.

*Flower buds.*—Shape: Lanceolate; pointed at apex. Length: About 8 mm. Diameter: About 2 mm. Color: 145C.

*Perianth.*—Aspect: Fan-shaped, flat. Length, fan: About 1.9 cm. Width, fan: About 2 cm.

*Petals.*—Quantity: Five, fused at base. Shape: Oblanceolate to linear. Apex: Mucronate. Margin: Entire. Length, above tube: About 8 mm. Width, above tube: About 2 mm. Length, tube: About 9 mm. Diameter, tube opening: About 3 mm. Texture, upper and lower surfaces: Smooth; flower throat, whiskered. Color, upper surface: N82C to N82D to N88C; towards base, N88D; color becoming closer to 92B with development. Color, lower surface and tube: N88C; towards the margins, 92C; center and towards base, 92D. Color, throat: 151C.

*Sepals.*—Quantity per flower: Five. Length: About 4 mm. Width: About 1 mm. Shape: Linear. Apex: Acute. Margin: Entire. Color, upper and lower surfaces: 141C.

*Reproductive organs.*—Androecium: Stamen quantity per flower: About five. Filament length: About 4 mm. Filament color: 1D. Anthers: Shape: Oblong. Length: About 1 mm. Color, immature: 165C. Color, mature: 165A. Pollen amount: Moderate. Pollen color: 2C. Gynoecium: Pistil quantity per flower: One. Pistil length: About 6 mm. Style length: About 5 mm. Style color: 149D overlain with 186D. Stigma shape: Flat, funnel-shaped. Stigma length: About 2 mm. Stigma color: Towards base, 143B; mid-section, 164A; towards apex, 144D. Ovary color: 149D.

*Seed/fruit.*—Seed and fruit production has not been observed.

Disease/pest resistance: Plants of the new Scaevola have been noted to be resistant to pathogens and pests common to Scaevola.

Temperature tolerance: Plants of the new Scaevola have been observed to be tolerant to temperatures ranging from 2 to 40° C.

It is claimed:

1. A new and distinct Scaevola plant named Balscavbon, as illustrated and described.

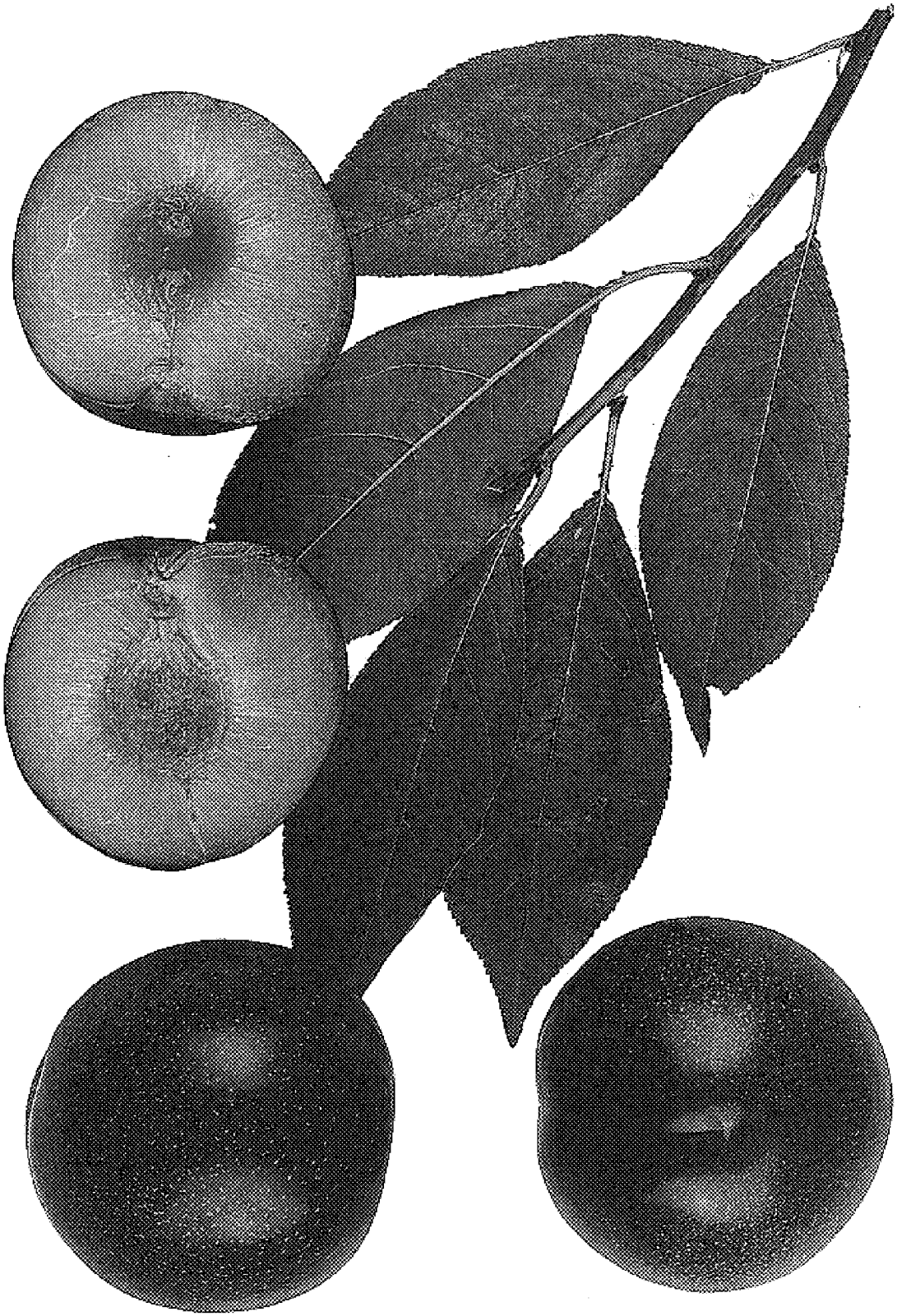

* * * * *